United States Patent
Ishizaki (10) Patent No.: US 10,110,824 B2
(45) Date of Patent: Oct. 23, 2018

(54) INSERTION DEVICE

(71) Applicant: OLYMPUS CORPORATION, Tokyo (JP)

(72) Inventor: Ryosuke Ishizaki, Fuchu (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/487,498

(22) Filed: Apr. 14, 2017

(65) Prior Publication Data

US 2017/0223278 A1 Aug. 3, 2017

Related U.S. Application Data

(63) Continuation of application No. PCT/JP2016/059724, filed on Mar. 25, 2016.

(30) Foreign Application Priority Data

Jun. 5, 2015 (JP) .................................. 2015-114888

(51) Int. Cl.
*A61B 1/00* (2006.01)
*H04N 5/232* (2006.01)
(Continued)

(52) U.S. Cl.
CPC ....... *H04N 5/23296* (2013.01); *A61B 1/0016* (2013.01); *A61B 1/00156* (2013.01);
(Continued)

(58) Field of Classification Search
CPC ......... F16H 7/02; F16H 57/01; A61B 1/0016; A61B 1/005; A61B 1/06; A61B 1/04; A61B 1/00156; A61B 1/31; G02B 23/2476

See application file for complete search history.

(56) References Cited

U.S. PATENT DOCUMENTS

2012/0029281 A1* 2/2012 Frassica ............. A61B 1/00082
600/114
2014/0323805 A1 10/2014 Naito

FOREIGN PATENT DOCUMENTS

EP 3 015 045 A1 5/2016
EP 3 069 649 A1 9/2016
(Continued)

OTHER PUBLICATIONS

English translation of International Preliminary Report on Patentability dated Dec. 14, 2017 together with the Written Opinion received in related International Application No. PCT/JP2016/059724.

(Continued)

*Primary Examiner* — Timothy J Neal
(74) *Attorney, Agent, or Firm* — Scully, Scott, Murphy & Presser, P.C.

(57) ABSTRACT

An insertion device includes a rotor rotating around a first revolution axis, and an assist tool attached to an insertion section with covering the rotor from an outer peripheral side. An assist tool rotates together with the rotor around a second revolution axis when press force is applied from a first protrusion of the rotor to a second protrusion of the assist tool by rotating of the rotor. The first revolution axis of the rotor and the second revolution axis of the assist tool move closer to each other when the rotor and the assist tool are rotating together.

5 Claims, 7 Drawing Sheets

(51) Int. Cl.
    *H01H 13/16*    (2006.01)
    *H04N 5/225*    (2006.01)
(52) U.S. Cl.
    CPC ......... *H01H 13/16* (2013.01); *A61B 1/00135* (2013.01); *H04N 5/2256* (2013.01); *H04N 2005/2255* (2013.01)

(56) References Cited

FOREIGN PATENT DOCUMENTS

| JP | 5586813 B1 | 9/2014 |
| WO | WO 2013/038720 A1 | 3/2013 |
| WO | WO 2014/208333 A1 | 12/2014 |
| WO | WO 2014/208334 A | 12/2014 |
| WO | WO 2015/019675 A1 | 2/2015 |
| WO | WO 2015/072233 A1 | 5/2015 |

OTHER PUBLICATIONS

International Search Report dated Jun. 21, 2016 issued in PCT/JP2016/059724.
Extended Supplementary European Search Report dated Jun. 8, 2018 in European Patent Application No. 16 80 2891.8.
Chinese Office Action dated Mar. 30, 2018 in Chinese Patent Application No. 201680003314.4.

* cited by examiner

INSERTION DEVICE

CROSS-REFERENCE TO RELATED APPLICATIONS

This is a Continuation Application of PCT Application No. PCT/JP2016/059724, filed Mar. 25, 2016 and based upon and claiming the benefit of priority from prior Japanese Patent Application No. 2015-114888, filed Jun. 5, 2015, the entire contents of which are incorporated herein by reference.

BACKGROUND OF THE INVENTION

1. Field of the Invention

The present invention relates to an insertion device in which a rotator provided in an insertion section rotates, whereby press force is applied to a second protrusion of an assist tool from a first protrusion of the rotator, and thus the assist tool attached to the insertion section rotates together with the rotor.

2. Description of the Related Art

In International Publication No. 2013/038720, a spiral unit (assist tool) attached to an insertion section of an endoscope (insertion instrument) is disclosed. The spiral unit which is removably attached to the insertion section in a state covering the insertion section from the outer peripheral side, and which includes a spiral fin spirally extended around a longitudinal axis. The insertion section is provided with a rotor, and the rotor is rotatably attached to a base portion of the insertion section around a first revolution axis (longitudinal axis). The rotor is provided with first rollers (first protrusions), and the spiral unit is provided with second rollers (second protrusions). When the rotor rotates around the first revolution axis (longitudinal axis) by the transmission of driving force thereto, press force is applied from each of the first rollers to the corresponding second roller in a rotating direction of the rotor. Due to the application of the press force from each of the first rollers to the corresponding second roller, the driving force is transmitted to the spiral unit, whereby the spiral unit rotates relative to the base portion around a second revolution axis (longitudinal axis) that is substantially coaxial with the first revolution axis of the rotor. The spiral unit rotates around the second revolution axis in a state where the spiral fin is pressed to the inner peripheral side, whereby propulsive force toward the distal side or the proximal side is applied to the insertion section and the spiral unit.

BRIEF SUMMARY OF THE INVENTION

According to one aspect of the invention, an insertion device including: an insertion section which extends from a proximal side to a distal side along a longitudinal direction; a rotor which is provided in the insertion section, and which is configured to rotate around a first revolution axis when driving force is transmitted thereto; a first protrusion which protrudes toward an outer peripheral side in the rotor; an assist tool which is attached to the insertion section in a state covering the rotor from the outer peripheral side; a second protrusion which protrudes toward an inner peripheral side in the assist tool, and which is configured to rotate the assist tool together with the rotor around a second revolution axis when press force is applied from the first protrusion by rotating of the rotor; and an axis adjustment unit which is configured to move the first revolution axis of the rotor and the second revolution axis of the assist tool closer to each other in a state where the rotor and the assist tool are rotating together.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
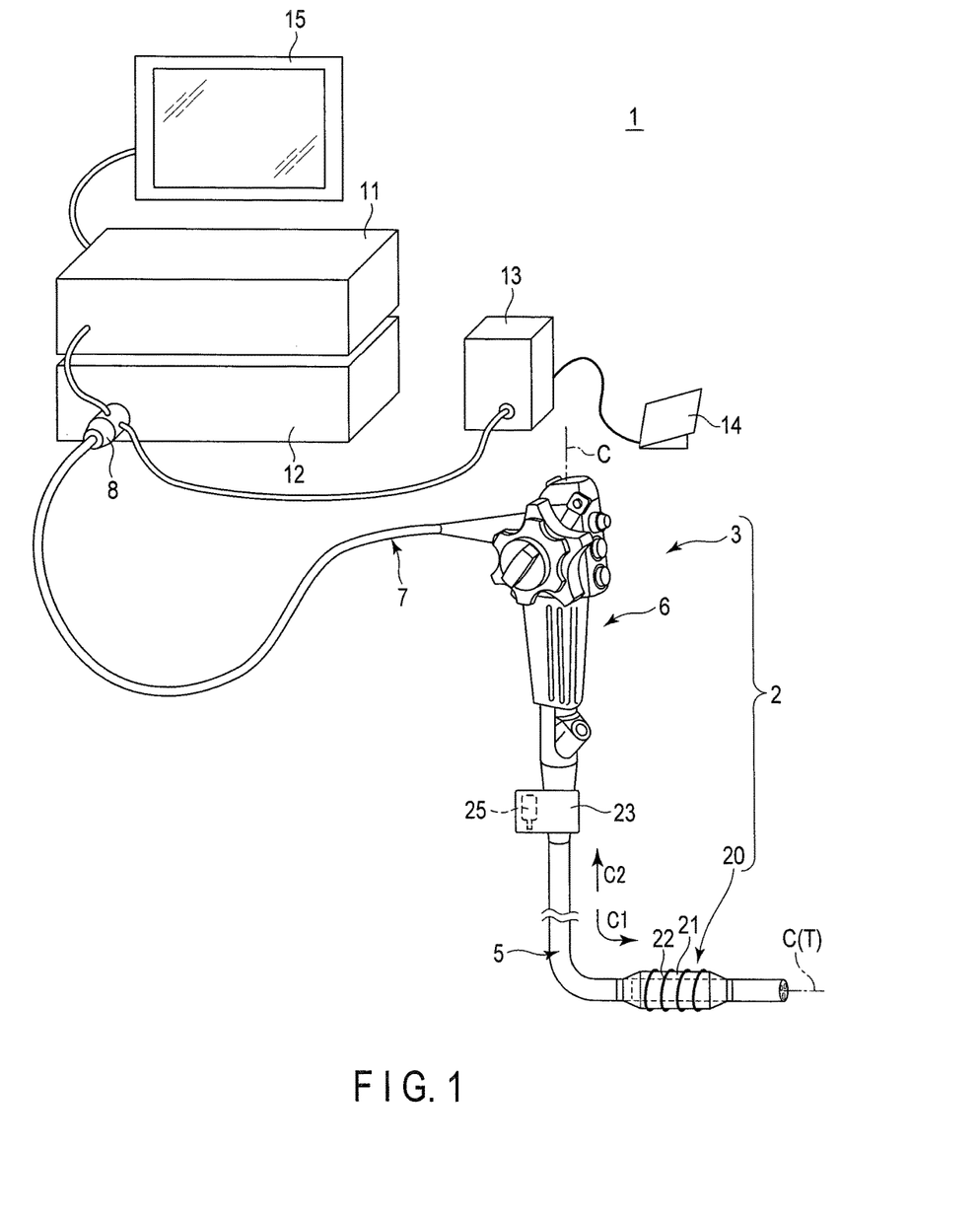
FIG. 1 is a perspective view schematically showing an endoscope system in which an endoscope device is used, according to a first embodiment.

A first embodiment of the present invention is described with reference to FIG. 1 to FIG. 10. FIG. 1 is a diagram showing an endoscope system 1 in which an endoscope device 2 that is an insertion device is used. As shown in FIG. 1, the endoscope device 2 includes an endoscope 3 which is an insertion instrument, and a spiral unit 20 which is an assist tool. The endoscope 3 includes an insertion section 5, and the insertion section 5 has a longitudinal axis C. Here, a direction along the longitudinal axis C is a longitudinal direction. Here, one side of the longitudinal direction is a distal side (an arrow C1 side in FIG. 1), and the side opposite to the distal side is a proximal side (an arrow C2 side in FIG. 1). The insertion section 5 extends from the proximal side to the distal side in the longitudinal direction, and an operation section 6 is provided on the proximal side of the insertion section 5 in the endoscope 3. The endoscope 3 includes a universal cord 7 having one end connected to the operation section 6. A scope connector 8 is provided at the other end of the universal cord 7.

As peripheral devices, the endoscope system 1 includes an image processing device 11 such as an image processor, a light source device 12 such as a lamp, a driving control device 13, an operation input device 14 such as a foot switch, and a display device 15 such as a monitor. The universal cord 7 is removably connected to the light source device 12 via the scope connector 8. In the endoscope 3, an imaging cable (not shown) and a light guide (not shown) extend through the inside of the insertion section 5, the inside of the operation section 6, and the inside of the universal cord 7. An imaging element (not shown) such as a CCD is provided inside the distal portion of the insertion section 5. The imaging element images a subject through an observation window (not shown) provided on the outer surface of the distal portion of the insertion section 5. An imaging signal is then transmitted to the image processing device 11 via the imaging cable, and image processing is performed in the image processing device 11. Thus, an image of the subject is generated in the image processing device 11, and the generated image of the subject is displayed on the display device 15. Light emitted from the light source device 12 is guided through the light guide. The guided light is then applied to the subject from an illumination window (not shown) provided on the outer surface of the distal portion of the insertion section 5.

In the endoscope device 2, the spiral unit 20 (assist tool) is removably attached to the insertion section 5 in a state where the insertion section 5 is inserted through the spiral unit 20. The spiral unit 20 has an extension axis T as a central axis. In a state where the spiral unit 20 is attached to the insertion section, the extension axis T is substantially parallel (substantially coaxial) with the longitudinal axis C of the insertion section 5. The spiral unit 20 includes a cylindrical tube main body 21 extending along the extension axis T (longitudinal axis C), and a spiral fin 22 protruding toward the outer peripheral side on the outer peripheral surface of the tube main body 21. The spiral fin 22 is spirally extended around the extension axis T. The spiral unit (assist tool) 20 is rotatable around the extension axis T which is substantially coaxial with the longitudinal axis C.

In the endoscope 3, a motor casing 23 is attached to the operation section 6. An electric motor 25 which is a driving member is provided inside the motor casing 23. One end of an electric wiring line (not shown) is connected to the electric motor 25. The electric wiring line is connected to the driving control device 13 through the inside of the operation section 6 and the inside of the universal cord 7. The driving control device 13 controls the supply state of driving electric power to the electric motor 25 on the basis of an operation input in the operation input device 14, and controls the driving state of the electric motor 25. A processor or the like including a central processing unit (CPU) or an application specific integrated circuit (ASIC) or the like, and a storage medium such as a memory are provided in the driving control device 13. The electric motor 25 is driven by the supply of the driving electric power to the electric motor 25, and driving force to rotate (revolve) the spiral unit 20 around the extension axis T is generated.

Figure 2:
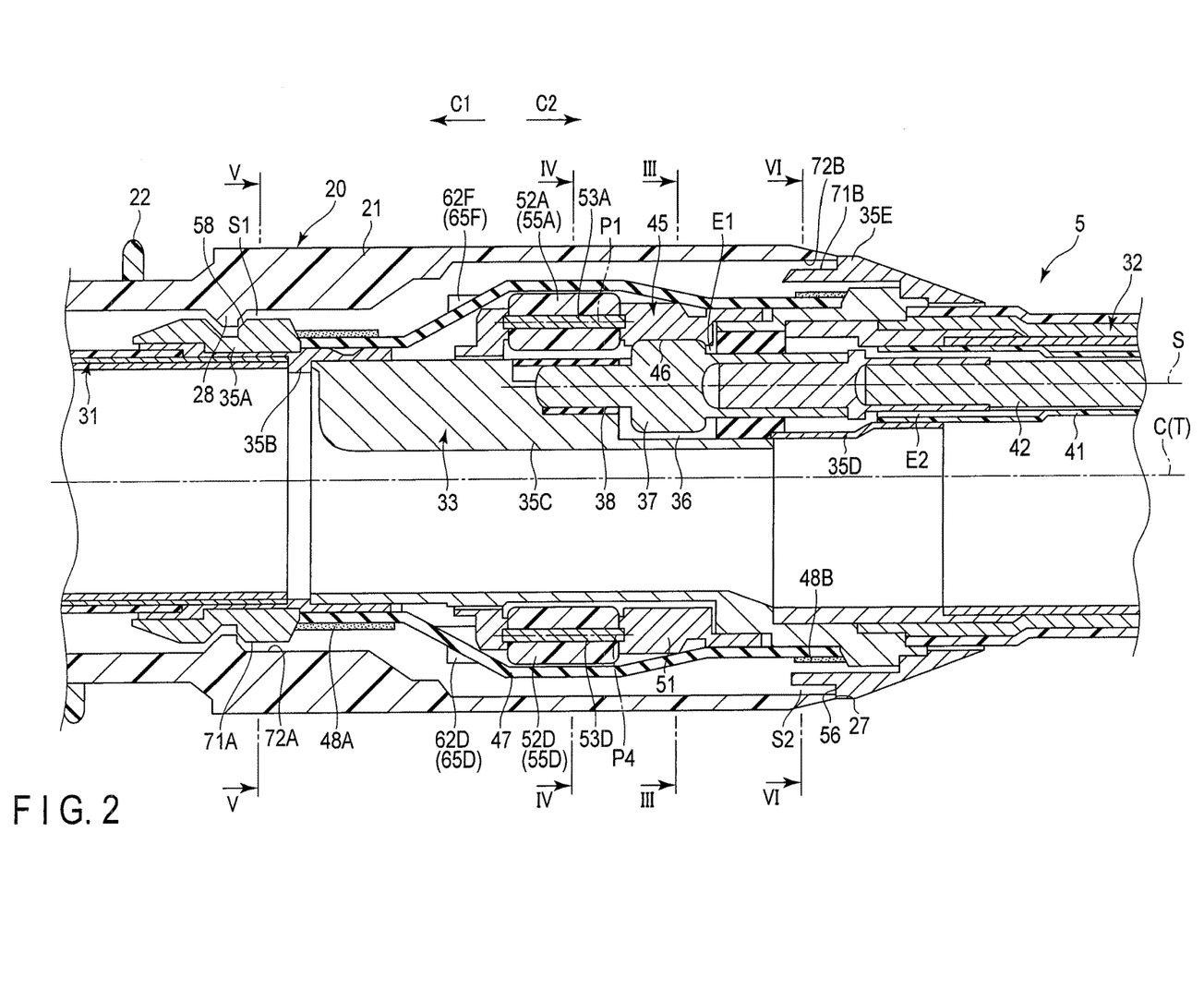
FIG. 2 is a sectional view schematically showing the configurations of the insertion section and the spiral unit in a portion to which a spiral unit is attached and in the vicinity of this portion in a state where the spiral unit is rotating, according to the first embodiment.

FIG. 2 is a diagram showing the configurations of the insertion section 5 and the spiral unit 20 in a portion to which the spiral unit is attached and in the vicinity of this portion. FIG. 2 shows a state where the spiral unit 20 is rotating around the extension axis T, and a state where the longitudinal axis (first revolution axis) C is coaxial with the extension axis (second revolution axis) T of the spiral unit 20. In FIG. 2, the imaging cable, the light guide, and others are omitted. As shown in FIG. 2, the insertion section 5 includes a distal side flexible tube section 31, and a proximal side flexible tube section 32 provided on the proximal side with respect to the distal side flexible tube section 31. The proximal end of the proximal side flexible tube section 32 is connected to the operation section 6. A base portion 33 made of a rigid material is provided between the distal side flexible tube section 31 and the proximal side flexible tube section 32. That is, the distal side flexible tube section 31 is coupled to the proximal side flexible tube section 32 via the base portion 33. In a state where the spiral unit 20 is attached to the insertion section 5, the outer peripheral side of the base portion 33 is covered with the proximal portion of the spiral unit 20, and the spiral unit 20 extends toward the distal side from a part on the outer peripheral side of the base portion 33. Although the base portion 33 is formed by the coupling of five coupling members 35A to 35E in the present embodiment, the number of members that form the base portion 33 is not limited to this, and, for example, the base portion 33 may be integrally formed from one member.

Figure 3:
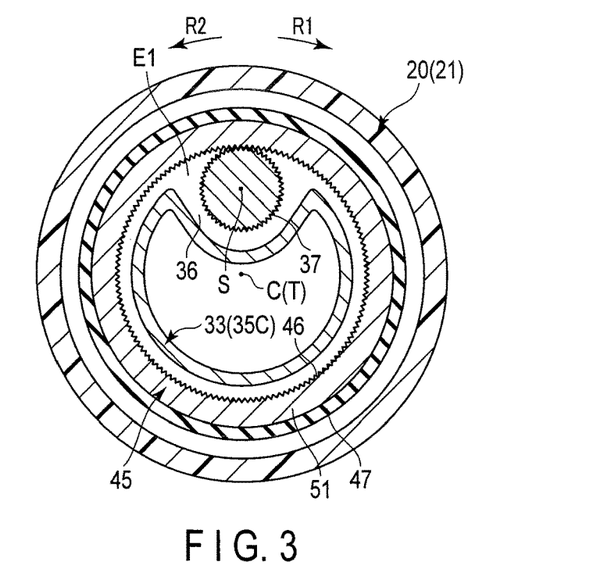
FIG. 3 is a sectional view taken along the line III-III in FIG. 2.
Figure 4:
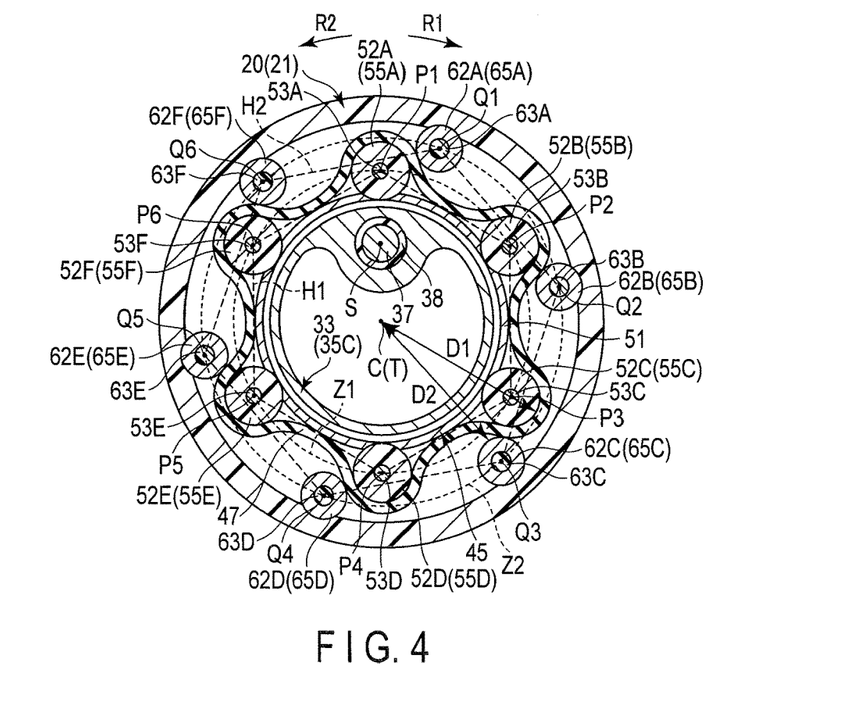
FIG. 4 is a sectional view taken along the line IV-IV in FIG. 2.

FIG. 3 is a sectional view taken along the line III-III in FIG. 2. FIG. 4 is a sectional view taken along the line IV-IV in FIG. 2. Therefore, FIG. 3 and FIG. 4 show sections perpendicular to the longitudinal axis C (extension axis T). As shown in FIG. 2 to FIG. 4, a cavity 36 is formed by the base portion 33 in the insertion section 5. The cavity 36 is open toward the outer peripheral side at a first opening position E1, and open at a second opening position E2 toward the space where the imaging cable, the light guide (both are not shown), and others extends. In the cavity 36, a driving gear 37 is attached to the base portion 33 (coupling member 35C) via a support member 38. Inside the proximal side flexible tube section 32, a channel tube 41 extends from the proximal side to the distal side. The distal end of the channel tube 41 is connected to the base portion 33 (coupling member 35D) at the second opening position E2. Inside the channel tube 41, a driving shaft 42 extends along a shaft axis S which is substantially parallel with the longitudinal axis C. The distal end of the driving shaft 42 is inserted into the cavity 36 from the second opening position E2, and connected to the driving gear 37. The proximal end of the driving shaft 42 is coupled to the electric motor 25 via a gear (not shown) or the like. When the electric motor 25 is driven, driving force is transmitted to the driving shaft 42, and the driving shaft 42 rotates around the shaft axis S. As a result, the driving force is transmitted to the driving gear 37, and the driving gear 37 rotates.

The insertion section 5 includes a cylindrical rotor 45 which is attached to the base portion 33 in a state covering the base portion 33 (coupling member 35C) from the outer peripheral side. The rotor 45 is rotatable relative to the base portion 33 around the longitudinal axis (first revolution axis) C. An inner peripheral gear portion 46 is provided on the inner peripheral surface of the rotor 45. The inner peripheral gear portion 46 extends over a whole round around the longitudinal axis C (around the first revolution axis). The driving gear 37 is in mesh with the inner peripheral gear portion 46 at the first opening position E1 of the cavity 36. Thus, the driving force is transmitted to the rotor 45 by the rotating of the driving gear 37, and the rotor 45 rotates around the longitudinal axis (first revolution axis) C.

The rotor 45 includes a cylindrical rotating member 51, and (in the present embodiment, six) first rollers (inner rollers) 52A to 52F attached to the cylindrical rotating member 51. Each of the first rollers 52A to 52F is attached to the cylindrical rotating member 51 via a corresponding first roller shaft (corresponding one of 53A to 53F). In the rotor 45, a corresponding first protrusion (corresponding one of 55A to 55F) is formed by each of the first rollers 52A to 52F. Each of the first protrusions (inner protrusions) 55A to 55F protrudes toward the outer peripheral side in the rotor 45, and has a first protrusion axis (corresponding one of P1 to P6) as a central axis. The first protrusion axes P1 to P6 are substantially parallel with the longitudinal axis C. In the present embodiment, each of the first roller shafts (inner roller shafts) 53A to 53F extends along the corresponding first protrusion axis (corresponding one of P1 to P6). Each of the first rollers 52A to 52F is rotatable (turnable) relative to the cylindrical rotating member 51 around the first protrusion axis (corresponding one of P1 to P6). That is, each of the first protrusion axes P1 to P6 is a rotation axis of the corresponding first roller (corresponding one of 52A to 52F).

The first protrusions 55A to 55F (the first rollers 52A to 52F) are provided apart from one another around the longitudinal axis C (around the first revolution axis), and in the present embodiment, the first protrusions 55A to 55F are arranged at substantially equal intervals around the longitudinal axis C. The relative position of each of the first protrusions 55A to 55F relative to the other first protrusions (corresponding five of 55A to 55F) is fixed, and all the first protrusions 55A to 55F move together by the movement of the rotor 45. Thus, when the driving force is transmitted to the rotor 45, each of the first protrusions 55A to 55F rotates around the longitudinal axis (first revolution axis) C together with the other first protrusions (corresponding five of 55A to 55F). If the first protrusion axis (corresponding one of P1 to P6) of each of the first protrusions 55A to 55F is connected by line to the first protrusion axes (corresponding two of P1 to P6) of the first protrusions (corresponding two of 55A to 55F) adjacently provided around the longitudinal axis C (around the first revolution axis), a hexagon H1 is formed as a polygon. In the present embodiment, the center (center of gravity) of the hexagon H1 is the longitudinal axis (first revolution axis) C. Therefore, the distance from the longitudinal axis C to each of the first protrusion axes P1 to P6 in the diametrical direction is the same as the distance from the longitudinal axis C to the other first protrusion axes (corresponding five of P1 to P6) in the diametrical direction.

In the insertion section 5, a cylindrical cover tube 47 which covers the rotor 45 from the outer peripheral side is provided. The cover tube 47 is made of, for example, rubber, and is flexible. A part of the outer surface of the insertion section 5 is formed by the cover tube 47. The distal end of the cover tube 47 is located on the distal side with respect to the distal end of the rotor 45, and fixed to the base portion 33 (coupling member 35B) by an adhesive member 48A. The proximal end of the cover tube 47 is located on the proximal side with respect to the proximal end of the rotor 45, and fixed to the base portion 33 (coupling member 35C) by an adhesive member 48B. At the distal end and proximal end of the cover tube 47, liquid tightness is maintained between the base portion 33 and the cover tube 47. This prevents the inflow of liquid from the outside of the insertion section 5 to the inner peripheral side of the cover tube 47, and prevents the inflow of liquid from the outside of the insertion section 5 to the part where the rotor 45 is disposed and to the cavity 36 where the driving gear 37 is disposed. The rotor 45 is rotatable relative to the cover tube 47 around the longitudinal axis (first revolution axis) C.

The spiral unit (assist tool) 20 is removably attached to the insertion section 5 in a state where the proximal portion of the spiral unit 20 covers the cover tube 47 from the outer peripheral side. Therefore, the cover tube 47 is disposed between the rotor 45 and the spiral unit 20 in a state covering the rotor 45 from the outer peripheral side. That is, in a state where the spiral unit (assist tool) 20 is attached to the insertion section 5, the spiral unit 20 is located on the outer peripheral side with respect to the rotor 45 and the cover tube 47, and the rotor 45 is located on the inner peripheral side with respect to the cover tube 47.

In the coupling member 35E of the base portion 33, a receiving surface 56 on which a proximal end face 27 of the spiral unit 20 (a proximal end face of the tube main body 21) can abut is formed. The receiving surface 56 is located on the proximal side with respect to the proximal end of the rotor 45. The proximal end face 27 of the spiral unit 20 abuts on the receiving surface 56, so that the movement of the spiral unit 20 to the proximal side from the receiving surface 56 is prevented.

An engagement groove 58 recessed toward the inner peripheral side is provided on the outer peripheral surface of the coupling member 35A of the base portion 33. The engagement groove 58 is located on the distal side with respect to the distal end of the rotor 45. The engagement groove 58 is formed over a whole circumference around the longitudinal axis C (around the first revolution axis). An engagement claw 28 which protrudes toward the inner peripheral side is provided on the inner peripheral surface of the spiral unit 20 (the tube main body 21). When the spiral unit 20 is attached to the insertion section 5, the engagement claw 28 engages with the engagement groove 58. This regulates the movement of the spiral unit 20 relative to the insertion section 5 along the longitudinal axis C in the longitudinal direction. Because the movement of the spiral unit 20 relative to the insertion section 5 in the longitudinal direction is regulated, detachment of the spiral unit 20 from the insertion section 5 is prevented in a state where the spiral unit 20 is rotating around the extension axis (second revolution axis) T which is substantially coaxial with the longitudinal axis C by the transmission of driving force thereto.

(In the present embodiment, six) second rollers (outer rollers) 62A to 62F attached to the inner peripheral surface of the tube main body 21 are provided in the proximal portion of the spiral unit 20. The second rollers 62A to 62F are located on the proximal side with respect to the engagement claw 28. Each of the second rollers 62A to 62F is attached to the tube main body 21 via a corresponding second roller shaft (corresponding one of 63A to 63F). In the spiral unit (assist tool) 20, a corresponding second protrusion (corresponding one of 65A to 65F) is formed by each of the second rollers 62A to 62F. Each of the second protrusions (outer protrusions) 65A to 65F protrudes toward the inner peripheral side in the spiral unit 20, and has a second protrusion axis (corresponding one of Q1 to Q6) as a central axis. The second protrusion axes Q1 to Q6 are substantially parallel with the extension axis T. In the present embodiment, each of the second roller shafts (outer roller shafts) 63A to 63F extends along the corresponding second protrusion axis (corresponding one of Q1 to Q6). Each of the second rollers 62A to 62F is rotatable (turnable) relative to the tube main body 21 around the corresponding second protrusion axis (corresponding one of Q1 to Q6). That is, each of the second protrusion axes Q1 to Q6 is a rotation axis of the corresponding second roller (corresponding one of 62A to 62F).

The second protrusions 65A to 65F (the second rollers 62A to 62F) are provided apart from one another around the extension axis T (around the second revolution axis), and in the present embodiment, the second protrusions 65A to 65F are arranged at substantially equal intervals around the extension axis T. In a state where the spiral unit 20 is attached to the insertion section 5, each of the second protrusions 65A to 65F is disposed between corresponding two of the first protrusions 55A to 55F around the extension axis T (around the longitudinal axis C), and for example, the second protrusion 65A is disposed between the first protrusion 55A and the first protrusion 55B around the extension axis T (around the longitudinal axis C).

Relative position of each of the second protrusions 65A to 65F relative to the other second protrusions (corresponding five of 65A to 65F) is fixed, and all the second protrusions 65A to 65F move together by the movement of the spiral unit (assist tool) 20. If the second protrusion axis (corresponding one of Q1 to Q6) of each of the second protrusions 65A to 65F is connected by line to the second protrusion axes (corresponding two of Q1 to Q6) of the second protrusions (corresponding two of 65A to 65F) adjacently provided around the extension axis T (around the longitudinal axis C), a hexagon H2 is formed as a polygon. In the present embodiment, the center (center of gravity) of the hexagon H2 is the extension axis (second revolution axis) T. Therefore, the distance from the extension axis T to each of the second protrusion axes Q1 to Q6 in the diametrical direction is the same as the distance from the extension axis T to the other second protrusion axes (corresponding five of Q1 to Q6) in the diametrical direction.

When the driving force is transmitted to the rotor 45 as described above and the rotor 45 rotates toward one side (an arrow R1 side in each of FIGS. 3 and 4) around the longitudinal axis C (around the first revolution axis), each of the first protrusions 55A to 52F applies press force to the corresponding second protrusion (corresponding one of 65A to 65F) in the rotating direction of the rotor 45 (in this case, clockwise around the longitudinal axis C in FIG. 4) via the cover tube 47. For example, the first protrusion 55A applies press force to the second protrusion 65A via the cover tube 47. Consequently, the second protrusions 65A to 65F receive the driving force from the rotor 45, and the spiral unit 20 rotates relative to the base portion 33 together with the rotor 45 toward one side around the extension axis T (around the second revolution axis).

When the rotor 45 rotates toward the other side (an arrow R2 side in each of FIGS. 3 and 4) around the longitudinal axis C, each of the first protrusions 55A to 55F applies press force to the corresponding second protrusion (corresponding one of 65A to 65F) different from that in the case where the rotor 45 rotates toward one side around the longitudinal axis C, in the rotating direction of the rotor 45 (in this case, counterclockwise around the longitudinal axis C in FIG. 4) via the cover tube 47. For example, the first protrusion 55A applies press force to the second protrusion 65F via the cover tube 47. Consequently, the second protrusions 65A to 65F receive the driving force from the rotor 45, and the spiral unit 20 rotates relative to the base portion 33 together with the rotor 45 toward the other side around the extension axis T (around the second revolution axis). When the driving force is transmitted to the spiral unit 20, each of the second protrusions 65A to 65F rotates around the extension axis (the second revolution axis) T together with the other second protrusions (corresponding five of 65A to 65F), the tube main body 21, and the spiral fin 22.

When the spiral unit 20 rotates around the extension axis T in a state where the spiral fin 22 is pressed to the inner peripheral side, propulsive force toward the distal side or the proximal side (one side in the longitudinal direction) is applied to the insertion section 5 and the spiral unit 20. In a state where the rotor 45 and the spiral unit 20 rotate together, the cover tube 47 does not rotate. However, in this instance, the corresponding first roller (corresponding one of 52A to 52F) rotates (turns) in each of the first protrusions 55A to 55F, so that friction between the first protrusions 55A to 55F (the first rollers 52A to 52F) and the cover tube 47 is reduced. Similarly, the corresponding second roller (corresponding one of 62A to 62F) rotates (turns) in each of the second protrusions 65A to 65F, so that friction between the second protrusions 65A to 65F (the second rollers 62A to 62F) and the cover tube 47 is reduced.

Figure 5:
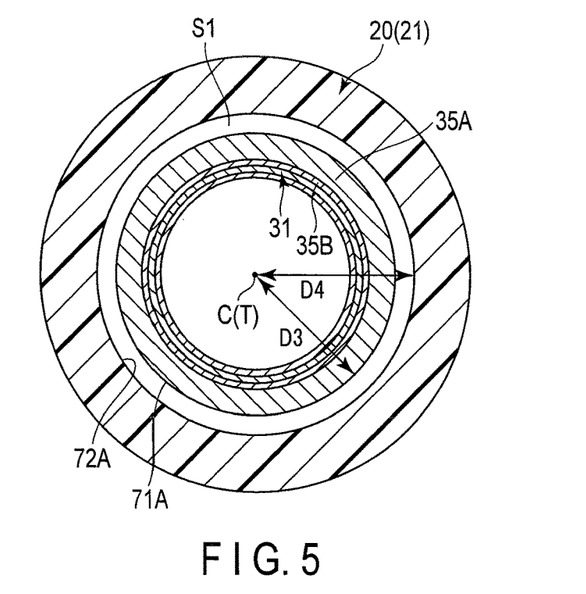
FIG. 5 is a sectional view taken along the line V-V in FIG. 2.
Figure 6:
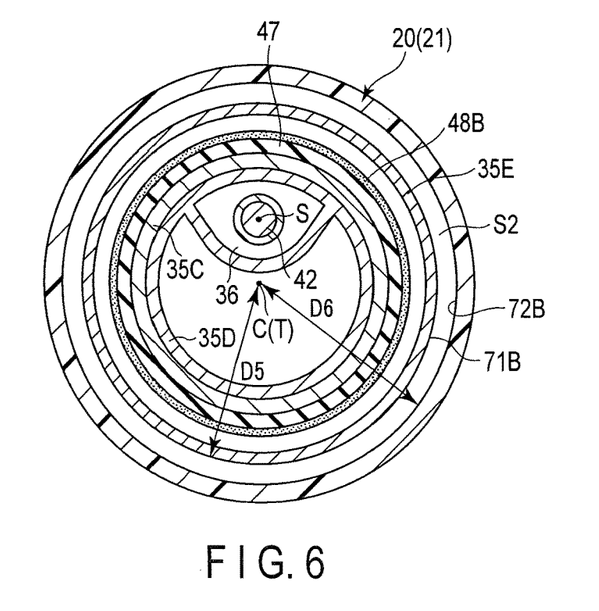
FIG. 6 is a sectional view taken along the line VI-VI in FIG. 2.
Figure 7:
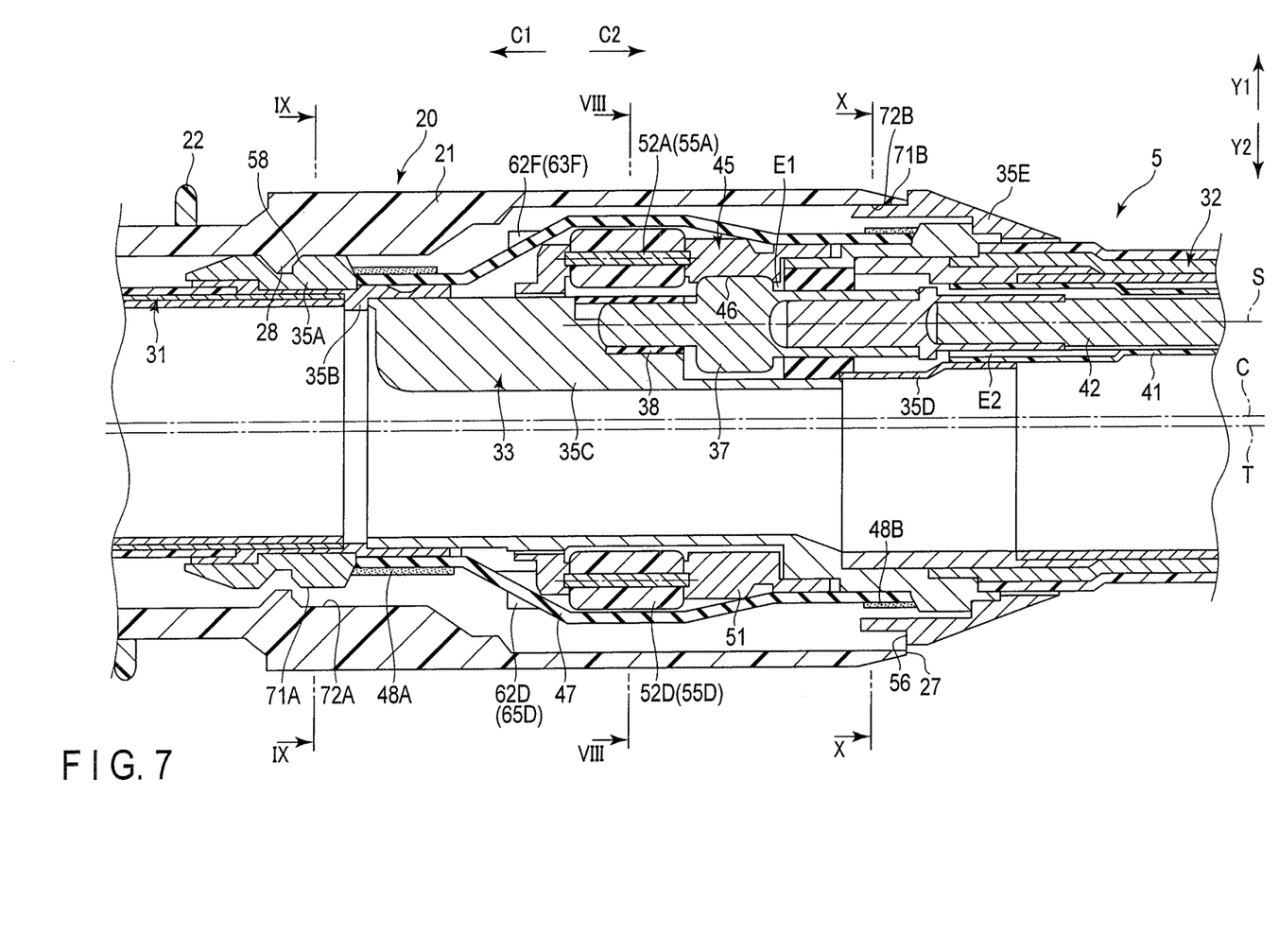
FIG. 7 is a sectional view schematically showing the configurations of the insertion section and the spiral unit in the portion to which the spiral unit is attached and in the vicinity of this portion in a state where the spiral unit is not rotating, according to the first embodiment.
Figure 8:
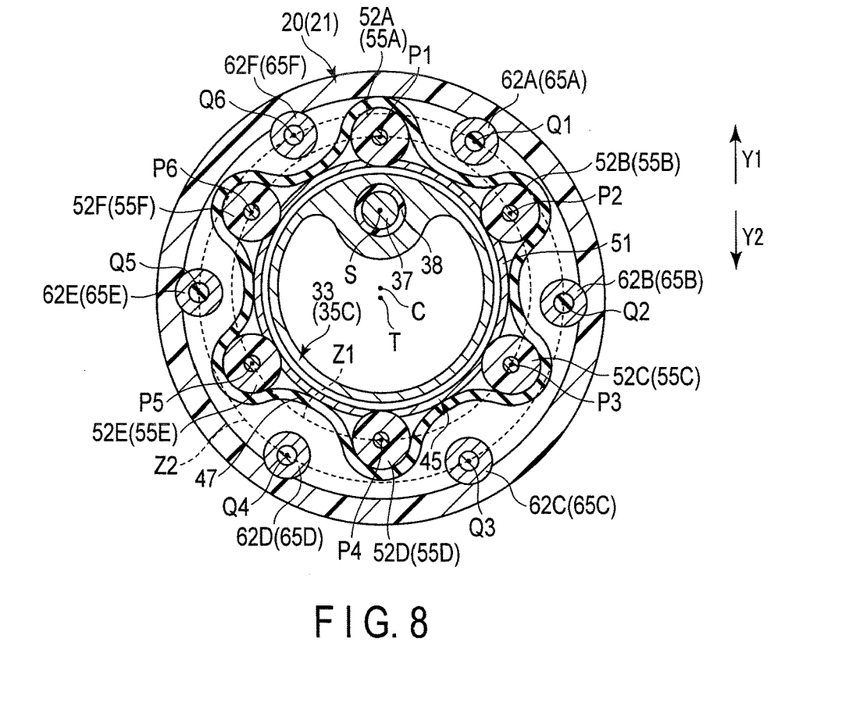
FIG. 8 is a sectional view taken along the line VIII-VIII in FIG. 7.
Figure 9:
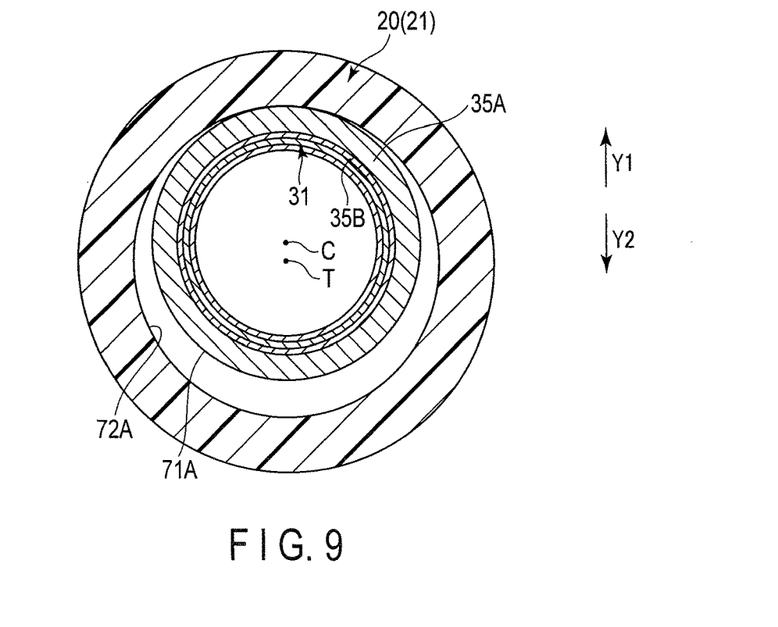
FIG. 9 is a sectional view taken along the line IX-IX in FIG. 7.
Figure 10:
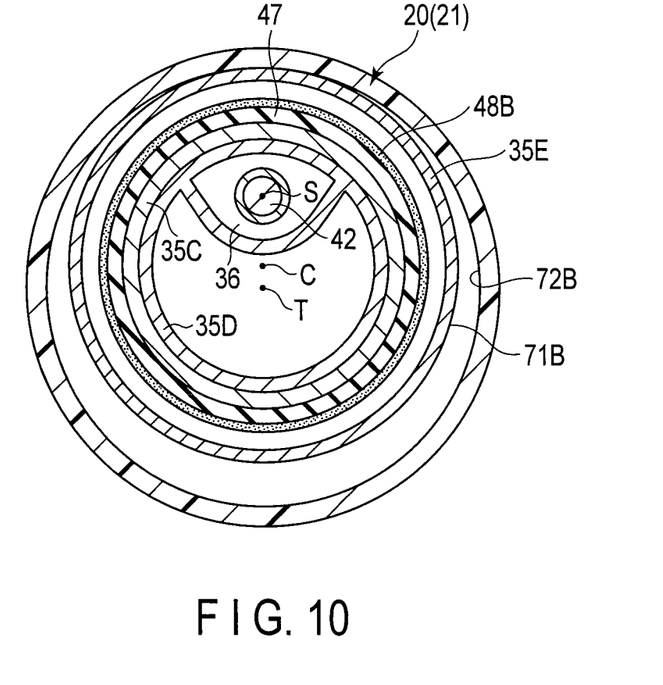
FIG. 10 is a sectional view taken along the line X-X in FIG. 7.

FIG. 5 is a sectional view taken along the line V-V in FIG. 2. FIG. 6 is a sectional view taken along the line VI-VI in FIG. 2. FIG. 7 is a diagram showing the configurations of the insertion section 5 and the spiral unit 20 in the portion to which the spiral unit is attached and in the vicinity of this portion in a state where the spiral unit 20 attached to the insertion section 5 is not rotating. FIG. 7 shows a state where the longitudinal axis (first revolution axis) C of the insertion section 5 and the extension axis (second revolution axis) T of the spiral unit 20 are located farthest from each other, and the imaging cable, the light guide, and others are omitted in FIG. 7. FIG. 8 is a sectional view taken along the line VIII-VIII in FIG. 7. FIG. 9 is a sectional view taken along the line IX-IX in FIG. 7. FIG. 10 is a sectional view taken along the line X-X in FIG. 7. In each of FIGS. 7 to 10, an arrow Y1 side is the upper side in the vertical direction, and an arrow Y2 side is the lower side in the vertical direction.

As shown in FIG. 2 and FIG. 7, on the outer peripheral surface of the base portion 33 (the outer peripheral surface of the coupling member 35A), a distal side supporting portion 71A on which the inner peripheral surface of the spiral unit (assist tool) 20 can abut is provided. On the inner peripheral surface of the spiral unit 20 (the inner peripheral surface of the tube main body 21), a distal side supported portion 72A which can abut on the distal side supporting portion 71A is provided. In a state where the spiral unit 20 is attached to the insertion section 5, the distal side supporting portion 71A and the distal side supported portion 72A are located on the distal side with respect to the first protrusions 55A to 55F of the rotor 45 and the second protrusions 65A to 65F of the spiral unit 20.

On the outer peripheral surface of the base portion 33 (the outer peripheral surface of the coupling member 35E), a proximal side supporting portion 71B on which the inner peripheral surface of the spiral unit (assist tool) 20 can abut is provided. On the inner peripheral surface of the spiral unit 20 (the inner peripheral surface of the tube main body 21), a proximal side supported portion 72B which can abut on the proximal side supporting portion 71B is provided. In a state where the spiral unit 20 is attached to the insertion section 5, the proximal side supporting portion 71B and the proximal side supported portion 72B are located on the proximal side with respect to the first protrusions 55A to 55F of the rotor 45 and the second protrusions 65A to 65F of the spiral unit 20.

The distal side supported portion 72A is supported to be able to abut on the distal side supporting portion 71A, and the proximal side supported portion 72B is supported to be able to abut on the proximal side supporting portion 71B, so that the extension axis (second revolution axis) T of the spiral unit 20 is regulated relative to the longitudinal axis (first revolution axis) C of the insertion section 5 (the rotor 45). In a state where the spiral unit 20 is attached to the insertion section 5, parts other than the distal side supported portion 72A (including the engagement claw 28) do not abut on the outer peripheral surface of the insertion section 5 in parts located on the distal side with respect to the second protrusions 65A to 65F of the spiral unit 20 whether or not the spiral unit 20 is rotating. In a state where the spiral unit 20 is attached to the insertion section 5, parts other than the proximal end face 27 and the proximal side supported portion 72B do not abut on the outer peripheral surface of the insertion section 5 in parts located on the proximal side with respect to the second protrusions 65A to 65F of the spiral unit 20 whether or not the spiral unit 20 is rotating.

As shown in FIG. 7 to FIG. 10, in a state where the spiral unit 20 attached to the insertion section 5 is not rotating, the extension axis (second revolution axis) T of the spiral unit 20 moves downward in the vertical direction apart from the longitudinal axis (first revolution axis) C of the rotor 45 (the insertion section 2) because of gravitation. As a result, the distal side supported portion 72A abuts on a part facing upward in the vertical direction in the distal side supporting portion 71A, and the proximal side supported portion 72B abuts on a part facing upward in the vertical direction in the proximal side supporting portion 71B. In a state where the distal side supported portion 72A abuts on the distal side supporting portion 71A and the proximal side supported portion 72B abuts on the proximal side supporting portion 71B, the longitudinal axis (first revolution axis) C of the insertion section 5 (the rotor 45) and the extension axis (second revolution axis) T of the spiral unit (assist tool) 20 are located farthest from each other (downward in the vertical direction).

As shown in FIG. 2 to FIG. 6, in a state where the spiral unit 20 attached to the insertion section 5 is rotating relative to the base portion 33 together with the rotor 45, a space S1 is formed in the diametrical direction between the distal side supporting portion 71A and the distal side supported portion 72A over a whole circumference around the extension axis T (around the second revolution axis), and a space S2 is formed in the diametrical direction between the proximal side supporting portion 71B and the proximal side supported portion 72B over an entire round around the extension axis T (around the second revolution axis). The size of the space S1 is determined by the dimension in the diametrical direction from the longitudinal axis C to the distal side supporting portion 71A and the dimension in the diametrical direction from the extension axis T to the distal side supported portion 72A, and is set in a predetermined range between a minimum value and a maximum value. Similarly, the size of the space S2 is determined by the dimension in the diametrical direction from the longitudinal axis C to the proximal side supporting portion 71B and the dimension in the diametrical direction from the extension axis T to the proximal side supported portion 72B, and is set in a predetermined range between a minimum value and a maximum value.

The minimum values of the spaces S1 and S2 are set on the basis of dimensional tolerances of members constituting the endoscope device 2, e.g., the base portion 33, the rotor 45, the first rollers 52A to 52F, the spiral units (the assistant tool) 20, the second rollers 62A to 62B, and the like, respectively. Thus, the sizes of the spaces S1 and S2 are set in correspondence with the dimensional tolerances of the members constituting the endoscope device 2, respectively. For example, it is assumed that a dimension from the longitudinal axis (the first revolution axis) C of the insertion section 5 to a projection end (an outer peripheral end) of each of the first protrusions 55A to 55F in a radial direction is D1 (see FIG. 4), and an outer radius dimension of the distal side supporting portion 71A is D3 (see FIG. 5). In the endoscope device 2, a deviation is produced between a central axis of the dimension D1 and a central axis of the outer radius dimension D3 (outer diameter) due to the dimensional tolerances of the first protrusions 55A to 55F and the distal side supporting portion 71A, and a maximum value of the deviation between the central axis of the dimension D1 and the central axis of the outer radius dimension D3 is assumed to be a first axis deviation maximum value δ1. Further, a dimension from the extension axis (the second revolution axis) T of the spiral unit 20 to a protrusion end (an inner peripheral end) of each of the second protrusions 65A to 65F in the radial direction is D2 (see FIG. 4), and an inner radius dimension of the distal side supported portion 72A is D4 (see FIG. 5). In the endoscope device 2, a deviation occurs between a central axis of the dimension D2 and a central axis of the inner radius dimension D4 (inner diameter) due to the dimensional tolerances of the second protrusions 65A to 65F and the distal side supported portion 72A, and a maximum value of the deviation between the central axis of the dimension D2 and the central axis of the inner radius dimension D4 is assumed to be a second axis deviation maximum value δ2. The above-described space S1 is set to be larger than a sum of the first axis deviation maximum value δ1 and the second axis deviation maximum value δ2. Furthermore, an outer radius dimension of the proximal side supporting portion 71B is assumed to be D5 (see FIG. 6). In the endoscope device 2, a deviation occurs between a central axis of the above-described dimension D1 and a central axis of the outer radius dimension D5 (outer diameter) due to the dimensional tolerances of the first protrusions 55A to 55F and the proximal side supporting portion 71B, and a maximum value of the deviation between the central axis of the dimension D1 and the central axis of the outer radius dimension D5 is assumed to be a third axis dimension maximum value δ3. Moreover, an inner radius dimension of the proximal side supported portion 72B is assumed to be D6 (see FIG. 6). In the endoscope device 2, a deviation occurs between a central axis of the above-described dimension D2 and a central axis of the inner radius dimension D6 (inner diameter) due to the dimensional tolerances of the second protrusions 65A to 65F and the proximal side supported portion 72B, and a maximum value of the deviation between the central axis of the dimension D2 and the central axis of the inner radius dimension D6 is assumed to be a fourth axis deviation maximum value δ4. The above-described space S2 is set to be larger than a sum of the third axis deviation maximum value δ3 and the fourth axis deviation maximum value δ4.

Here, it is assumed that a rotating orbit through which the first protrusion axes P1 to P6 of all the first protrusions 55A to 55F run in a state where the rotor 45 rotates around the longitudinal axis (the first revolution axis) C is a first rotating orbit Z1, and that a rotating orbit through which the second protrusion axes Q1 to Q6 of all the second protrusions 65A to 65F run in a state where the spiral unit 20 rotates around the extension axis (the second revolution axis) T is a second rotating orbit Z2. The maximum values of the spaces S1 and S2 are set on the basis of the first rotating orbit Z1 through which the first protrusion axes P1 to P6 run and the second rotating orbit Z2 through which the second protrusion axes Q1 to Q6 run in a state where the longitudinal axis (the first revolution axis) C and the extension axis (the second revolution axis) T have the greatest gap therebetween, respectively. That is, since the sizes of the spaces S1 and S2 are set in a predetermined range including the maximum values respectively, as shown in FIG. 8, even in a state where the longitudinal axis C of the insertion section 5 (the rotor 45) and the extension axis T of the spiral unit 20 have the greatest gap therebetween, the second rotating orbit Z2 through which the second protrusion axes Q1 to Q6 run does not cross the first rotating orbit Z1 through which the first protrusion axes P1 to P6 run, and it is placed on an outer peripheral side with respect to the first rotating orbit Z1 over an entire circumference around the extension axis T (around the second revolution axis).

Since each of the sizes of the spaces S1 and S2 is set in the predetermined range which is not smaller than the minimum value and not greater than the maximum value, when the spiral unit 20 attached to the insertion section 5 rotates together with the rotor 45, the longitudinal axis (the first revolution axis) C of the rotor 45 and the extension axis (the second revolution axis) T of the spiral unit 20, which are separated from each other, move closer to each other. That is, in a state where the rotor 45 and the spiral unit (assist tool) are rotating together, the distal side supporting portion 71A, the distal side supported portion 72A, the proximal side supporting portion 71B, and the proximal side supported portion 72B form an axis adjustment unit which moves the longitudinal axis (the first revolution axis) C of the rotor 45 and the extension axis (the second revolution axis) T of the spiral unit 20 closer to each other. The axis adjustment unit (71A, 71B, 72A, 72B) holds the longitudinal axis C which is a rotating axis of the rotor 45 and the extension axis T which is the rotation axis of the spiral unit 20 to be substantially coaxial with each other in the state where the rotor 45 and the spiral unit 20 are rotating together.

Next, functions and effects of the endoscope device 2 which is the insertion device according to the present invention will now be described. At the time of observing a lumen by using the endoscope device 2, the spiral unit (the assist tool) 20 is attached to the insertion section 5, and the insertion section 5 and the spiral unit 20 are inserted into the lumen. At this time, since the spiral unit 20 is not rotating, for example, as shown in FIG. 7 to FIG. 10, the extension axis (the second revolution axis) T of the spiral unit 20 is separated from the longitudinal axis (the first revolution axis) C of the rotor 45 (the insertion section 2) toward a lower side in a vertical direction due to a function of the gravity or the like. Consequently, the distal side supported section 72A abuts on a region of the distal side supporting section 71A which faces an upper side in the vertical direction, and the proximal side supported section 72B abuts on a region of the proximal side supporting portion 71B which faces the upper side in the vertical direction. Here, in this embodiment, a dimension from the longitudinal axis C to each of the distal side supporting portion 71A and the proximal side supporting portion 71B in the diametrical direction and a dimension from the extension axis T to each of the distal side supported portion 72A and the proximal side supported portion 72B in the diametrical direction are determined as described above. Thus, even if the extension axis T of the spiral unit 20 is separated from the longitudinal axis C of the insertion section 5 (the rotor 45) toward the lower side in the vertical direction, the second rotating orbit Z2 through which the second protrusion axes Q1 to Q6 run does not cross the first rotating orbit Z1 through which the first protrusion axes P1 to P6 run, and it is placed on the outer peripheral side with respect to the first rotating orbit Z1 over the entire round around the extension axis T (around the second revolution axis).

Additionally, on the basis of an operation input in the operation input device 14, the electric motor 25 is driven, and the driving force is transmitted to the spiral unit 20 as described above. Consequently, the spiral unit 20 rotates around the longitudinal axis (the revolution axis) C. In a state where the spiral fin 22 is pressed toward the inner peripheral side by a lumen wall, when the spiral unit 20 rotates, propulsive force to the distal side or the proximal side (one side of directions parallel to the longitudinal axis C) is applied to the insertion section 5 and the spiral unit 20. The propulsive force improves mobility of the insertion section 5 in the lumen.

Even if the extension axis T of the spiral unit 20 is separated from the longitudinal axis C of the insertion section 5 (the rotor 45) toward the lower side in the vertical direction, the second rotating orbit Z2 through which the second protrusion axes Q1 to Q6 run is placed on the outer peripheral side with respect to the first rotating orbit Z1 through which the first protrusion axes P1 to P6 run over the entire circumference around the extension axis T (around the second revolution axis). Thus, since the rotor 45 rotates around the longitudinal axis C and the press force is applied to the corresponding second protrusion (corresponding one of 65A to 65F) from each of the first protrusions 55A to 55F, the spiral unit 20 rotates around the extension axis T and also moves upward in the vertical direction. At this time, all the second protrusions 65A to 65F move together, and relative positions of each of the second protrusions 65A to 65F to the other second protrusions (corresponding five of 65A to 65F) do not change. Since the spiral unit 20 moves upward in the vertical direction, the extension axis T of the spiral unit 20 also moves upward in the vertical direction, and the longitudinal axis (the first revolution axis) C of the rotor 45 and the extension axis (the second revolution axis) T of the spiral unit 20, which are separated from each other, move closer to each other. It is to be noted that, if the first rotating orbit Z1 crosses the second rotating orbit Z2, the second protrusions 65A to 65F are not pushed toward the upper side (the outer peripheral side) in the vertical direction even though the first protrusions 55A to 55F rotate. Thus, this problem is solved by specifying the respective maximum values of the spaces S1 and S2 as described above.

The sizes of the spaces S1 and S2 in the radial direction are set in correspondence with the dimensional tolerances of the members constituting the endoscope device 2 as described above.

Thus, in this embodiment, in a state where the spiral unit 20 is rotating together with the rotor 45 to the base portion 33, axis adjustment (alignment) to move the longitudinal axis C of the rotor 45 and the extension axis T of the spiral unit 20 closer to each other, namely, to make the longitudinal axis (the first revolution axis) C and the extension axis (the second revolution axis) T substantially coaxial with each other is performed.

As described above, in this embodiment, since the axis adjustment to move the longitudinal axis C of the rotor 45 and the extension axis T of the spiral unit 20 closer to each other is performed in the state where the spiral unit 20 is rotating together with the rotor 45 relative to the base portion 33, each of the first protrusions 55A to 55F is arranged at an intended position relative to a corresponding second protrusion (corresponding one of 65A to 65F) to which the press force is applied. Thus, when the press force is applied from each of the first protrusions 55A to 55F of the rotor 45 to the corresponding second protrusion (corresponding one of 65A to 65F) of the spiral unit (the assist tool) 20, lines each connecting a central axis of one of the first protrusions 55A to 55F with a central axis of the corresponding second protrusion (corresponding one of 65A to 65F) and lines each connecting the central axis of one of the first protrusions 55A to 55F with the longitudinal axis (the first revolution axis) C form a uniform intersection angle at six positions, the press force is uniformly applied to all the second protrusions 65A to 65F, and there is no position on the spiral unit 20 on which the force is concentrated. Consequently, damage to the first protrusions 55A to 55F (the first rollers 52A to 52F) and the second protrusions 65A to 65F (the second rollers 62A to 62F) can be effectively avoided, and durability of the rotor 45 and the spiral unit 20 can be improved. Further, since the press force (torque) is uniformly applied to all the second protrusions 65A to 65F, the driving force is appropriately transmitted to the spiral unit 20 from the rotor 45, and the spiral unit 20 appropriately is actuated (rotates).

Furthermore, in a state where the spiral unit 20 is rotating together with the rotor 45 to the base portion 33, the cover tube 47 fixed to the base portion 33 is sandwiched between each of the first protrusions 55A to 55F of the rotor 45 and the corresponding second protrusion (corresponding one of 65A to 65F) of the spiral unit (the assist tool) 20. At this time, since the axis adjustment to move the longitudinal axis C of the rotor 45 and the extension axis T of the spiral unit 20 closer to each other is performed, force sandwiched between the first protrusions 55A to 55F and the second protrusions 65A to 65F is uniformly applied to the cover tube 47 at six positions around the longitudinal axis C (around the extension axis T), and there is no position on the cover tube 47 where the force is concentrated. Thus, damage to the cover tube 47 is effectively avoided, and the durability of the cover tube 47 is improved. Furthermore, since the force is uniformly applied to the cover tube 47 around the longitudinal axis C (around the extension axis T), rotating of the first protrusions 55A to 55F around the longitudinal axis C and rotating of the second protrusions 65A to 65F around the extension axis T are effectively prevented from being inhibited by the cover tube 47.

Modification

It is to be noted that, in the first embodiment, the corresponding rotatable first roller (corresponding one of 52A to 52F) is provided to each of the first protrusions 55A to 55F, and the corresponding rotatable second roller (corresponding one of 62A to 62F) is provided to each of the second protrusions 65A to 65F, but it is not restricted thereto. For example, in one modification, rotatable rollers are not provided to the first protrusions 55A to 55F, and the first protrusions 55A to 55F are integrally formed with the cylindrical rotating member 51. Moreover, rotatable rollers are not provided to the second protrusions 65A to 65F, and the second protrusions 65A to 65F are integrally formed with the tube main body 21.

Additionally, the number of the first protrusions (inner protrusions) 55A to 55F and the number of the second protrusions (outer protrusions) are not restricted to those in the foregoing embodiment. In one modification, three first protrusions (e.g., 55A to 55C) are provided in the rotor 45 around the longitudinal axis C at substantially equal intervals, and connecting by line a first protrusion axis (corresponding one of P1 to P3) of each of the first protrusions 55A to 55C with the first protrusion axes (corresponding two of P1 to P3) of the adjacent first protrusions (corresponding two of 55A to 55C) around the longitudinal axis C (around the first revolution axis) enables forming a triangle as a polygon. Further, a center (the centroid) of the triangle serves as the longitudinal axis (the first revolution axis) C. Furthermore, three second protrusions (e.g., 65A to 65C) are provided in the spiral unit 20 around the extension axis T at substantially equal intervals, and connecting by line a second protrusion axis (corresponding one of Q1 to Q3) of each of the second protrusions 65A to 65C with second protrusion axes (corresponding two of Q1 to Q3) of the adjacent second protrusions (corresponding two of Q1 to Q3) around the extension axis T (around the second revolution axis) enables forming a triangle as a polygon. Moreover, a center (the centroid) of the triangle serves as the extension axis (the second revolution axis) T.

That is, in case of a configuration where the three or more first protrusions (55A to 55F; 55A to 55C) are provided in the rotor 45, the polygon can be formed by the first protrusions (55A to 55F; 55A to 55C), and the first revolution axis (C) of the rotor 45 can be defined. Likewise, in case of a configuration where the three or more second protrusions (65A to 65F; 65A to 65C) are provided in the spiral unit (the assist tool) 20, the polygon can be formed by the second protrusions (65A to 65F; 65A to 65C), and the second revolution axis (T) of the spiral unit 20 is defined.

Additionally, in the foregoing embodiment or the like, the spiral unit (20) has been described as an example of the assist tool attached to the insertion section (5), but the assist tool is not restricted to the spiral unit (20). Further, in the foregoing embodiment or the like, the endoscope (2) has been described as an example of the insertion instrument, but the insertion instrument is not restricted to the endoscope (2). For example, the above-described configuration may be applied to an insertion operation system using a manipulator as the insertion instrument.

Furthermore, in a given modification, the cover tube (47) does not have to be provided between the rotor (45) and the assist tool (20). In this case, when the rotor (45) rotates around the first revolution axis (C), each of the first protrusions (55A to 55F) comes into contact with a corresponding second protrusion (corresponding one of 65A to 65F). Consequently, the press force is applied from each of the first protrusions (55A to 55F) to the corresponding second protrusion (corresponding one of 65A to 65F) in a rotating direction of the rotor (45), and the assist tool (20) rotates around the second revolution axis (T).

In the foregoing embodiment or the like, the insertion device (2) includes the insertion section (5) which extends from the proximal side (C2) to the distal side (C1) in the longitudinal direction, the rotor (45) which is provided in the insertion section (5), and which rotates around the first revolution axis (C) when the driving force is transmitted thereto, and the assist tool (20) attached to the insertion section (5) in a state covering the rotor (45) from the outer peripheral side. The first protrusions (55A to 55F) protruding toward the outer peripheral side are provided in the rotor (45), and the second protrusions (65A to 65F) protruding toward the inner peripheral side are provided in the assist tool (20). When the press force is applied to the second protrusions (65A to 65F) from the first protrusions (55A to 55B) by rotating of the rotor (45), the assist tool (20) rotates together with the rotor (45) around the second revolution axis (T). In a state where the rotor (45) and the assist tool (20) rotate together with each other, the axis adjustment unit (71A, 71B, 72A, 72B) move the first revolution axis (C) of the rotor (45) and the second revolution axis (T) of the assist tool (20) closer to each other.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
    an insertion section which extends from a proximal side to a distal side along a longitudinal direction, and which includes a base portion;
    a rotor which is attached to the base portion of the insertion section, and which is configured to rotate around a first revolution axis when driving force is transmitted thereto;
    a first protrusion which protrudes toward an outer peripheral side in the rotor;
    an assist tool which is attached to the insertion section in a state covering the rotor from the outer peripheral side;
    a second protrusion which protrudes toward an inner peripheral side in the assist tool, and which is configured to rotate the assist tool together with the rotor around a second revolution axis when press force is applied from the first protrusion by rotating of the rotor; and
    an axis adjustment unit which is configured to move the first revolution axis of the rotor and the second revolution axis of the assist tool closer to each other in a state where the rotor and the assist tool are rotating together,
    wherein the axis adjustment unit includes:
        a distal side supporting portion which is provided on the distal side with respect to the first protrusion on an outer peripheral surface of the base portion, and on which an inner peripheral surface of the assist tool is abuttable;
        a proximal side supporting portion which is provided on the proximal side with respect to the first protrusion on the outer peripheral surface of the base portion, and on which the inner peripheral surface of the assist tool is abuttable;
        a distal side supported portion which is provided on the distal side with respect to the second protrusion on the inner peripheral surface of the assist tool, and which is abuttable on the distal side supporting portion, the distal side supported portion having a space between itself and the distal side supporting portion in a radial direction over an entire circumference around the second revolution axis in the state where the rotor and the assist tool are rotating together; and
        a proximal side supported portion which is provided on the proximal side with respect to the second protrusion on the inner peripheral surface of the assist tool, and which is abuttable on the proximal side supporting portion, the proximal side supported portion having a space between itself and the proximal side supporting portion in the radial direction over the entire circumference around the second revolution axis in the state where the rotor and the assist tool are rotating together.

2. The insertion device according to claim 1, wherein, when a first axis deviation maximum value is given as a maximum value of a deviation between a central axis of a dimension from the first revolution axis to a protrusion end of the first protrusion in the radial direction and a central axis of an outer diameter of the distal side supporting portion, and when a second axis deviation maximum value is given as a maximum value of a deviation between a central axis of a dimension from the second revolution axis to a protrusion end of the second protrusion in the radial direction and a central axis of an inner diameter of the distal side supported portion, the space between the distal side supporting portion and the distal side supported portion in the radial direction is set to be larger than a sum of the first axis deviation maximum value and the second axis deviation maximum value, and
when a third axis deviation maximum value is given as a maximum value of a deviation between the central axis of the dimension from the first revolution axis to the protrusion end of the first protrusion in the radial direction and a central axis of an outer diameter of the proximal side supporting portion, and when a fourth axis deviation maximum value is given as a maximum value of a deviation between the central axis of the dimension from the second revolution axis to the protrusion end of the second protrusion in the radial direction and a central axis of an inner diameter of the proximal side supported portion, the space between the proximal side supporting portion and the proximal side supported portion in the radial direction is set to be larger than a sum of the third axis deviation maximum value and the fourth axis deviation maximum value.

3. The insertion device according to claim 1, wherein the first revolution axis of the rotor and the second revolution axis of the assist tool has the greatest gap therebetween in a state where the distal side supported portion abuts on the distal side supporting portion and the proximal side supported portion abuts on the proximal side supporting portion, and
when a first rotating orbit is given as a rotating orbit of a first protrusion axis, which is a central axis of the first protrusion, in a state where the rotor rotates around the first revolution axis, and when a second rotating orbit is given as a rotating orbit of a second protrusion axis, which is a central axis of the second protrusion, in a state where the assist tool rotates around the second revolution axis, the second rotating orbit does not cross the first rotating orbit and is placed on the outer peripheral side with respect to the first rotating orbit over an entire circumference around the second revolution axis even in a state where the first revolution axis and the second revolution axis have the greatest gap therebetween.

4. The insertion device according to claim 1, wherein three or more second protrusions are provided in the assist tool in a state where they are apart from each other around the second revolution axis,
a relative position of each of the second protrusions relative to the other second protrusions is fixed, and
all the second protrusions move together when the assist tool moves.

5. The insertion device according to claim 1, wherein the insertion section includes a cover tube which is provided between the rotor and the assist tool in a state covering the rotor from the outer peripheral side, and which has flexibility, and
the first protrusion applies the press force to the second protrusion through the cover tube.

* * * * *